(12) United States Patent
Gliner

(10) Patent No.: US 10,085,808 B2
(45) Date of Patent: Oct. 2, 2018

(54) ADJUSTABLE TRACKING SENSOR SUITABLE FOR DIFFERENT RIGID TOOLS

(71) Applicant: Biosense Webster (Israel) Ltd., Yokneam (IL)

(72) Inventor: Vadim Gliner, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 14/986,179

(22) Filed: Dec. 31, 2015

(65) Prior Publication Data
US 2017/0189122 A1    Jul. 6, 2017

(51) Int. Cl.
| | |
|---|---|
| G01R 27/08 | (2006.01) |
| A61B 34/20 | (2016.01) |
| A61B 34/00 | (2016.01) |
| G01B 7/12 | (2006.01) |
| G01B 7/14 | (2006.01) |
| A61B 17/00 | (2006.01) |
| A61B 90/00 | (2016.01) |

(52) U.S. Cl.
CPC ............ *A61B 34/20* (2016.02); *A61B 34/70* (2016.02); *G01B 7/12* (2013.01); *G01B 7/14* (2013.01); *A61B 2017/00477* (2013.01); *A61B 2034/2046* (2016.02); *A61B 2034/2051* (2016.02); *A61B 2034/2059* (2016.02); *A61B 2034/2068* (2016.02); *A61B 2034/2072* (2016.02); *A61B 2034/2074* (2016.02); *A61B 2090/061* (2016.02); *A61B 2090/3983* (2016.02); *A61B 2562/16* (2013.01)

(58) Field of Classification Search
CPC ......... A61B 34/09; A61B 34/20; A61B 34/25; A61B 34/70; A61B 18/14; A61B 18/12; A61B 17/24; G01B 7/12; G01B 7/14; G01B 7/003; G01B 7/023; G01L 1/205; G01R 27/02; G01R 27/32; G01R 27/28; B60R 21/015; B60R 2021/01516; G01N 27/041; G01N 27/9046
USPC ....... 324/691, 693, 699, 525, 600, 722, 724, 324/715, 716
See application file for complete search history.

(56) References Cited

U.S. PATENT DOCUMENTS

| | | | |
|---|---|---|---|
| 7,749,240 B2 * | 7/2010 | Takahashi ........ | A61B 17/32006 604/22 |
| 2003/0004434 A1 * | 1/2003 | Greco .................... | A61B 5/205 600/561 |
| 2004/0073138 A1 * | 4/2004 | Greco .................... | A61B 5/205 600/561 |

(Continued)

OTHER PUBLICATIONS

European Search Report dated May 29, 2017, Application No. EP 16 20 7597.

*Primary Examiner* — Thang Le

(57) ABSTRACT

Apparatus, including a rigid gripper configured to fasten around a cylindrical object. The apparatus further includes a pair of conductors attached to the gripper so as to make contact with one another, while the gripper is fastened around the cylindrical object, at a location along a length of the conductors that varies responsively to a diameter of the cylindrical object. The apparatus also includes a sensing circuit configured to measure an impedance of a current passing through the pair of conductors and to generate an indication of the diameter responsively to the impedance.

14 Claims, 10 Drawing Sheets

(56) References Cited

U.S. PATENT DOCUMENTS

| | | | |
|---|---|---|---|
| 2006/0173381 A1* | 8/2006 | Eck | A61M 25/00 |
| | | | 600/585 |
| 2007/0016009 A1 | 1/2007 | Lakin et al. | |
| 2008/0200794 A1 | 8/2008 | Teichman et al. | |
| 2009/0163930 A1 | 6/2009 | Aoude et al. | |
| 2010/0136854 A1* | 6/2010 | Gathman | H01R 11/24 |
| | | | 439/759 |
| 2010/0148756 A1* | 6/2010 | Shah | G01R 1/22 |
| | | | 324/126 |
| 2015/0045649 A1* | 2/2015 | O'Dea | A61B 5/6853 |
| | | | 600/409 |

\* cited by examiner

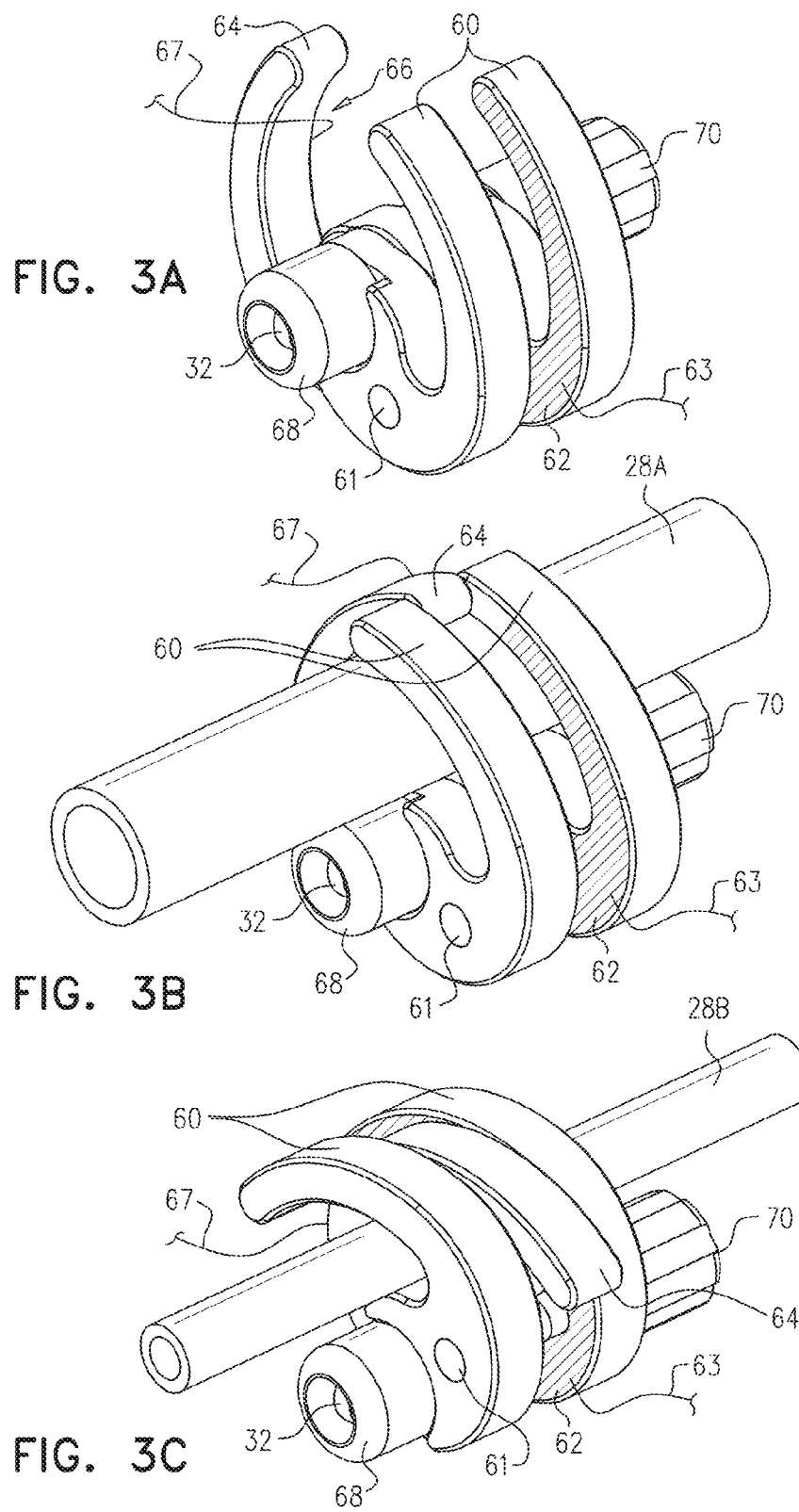

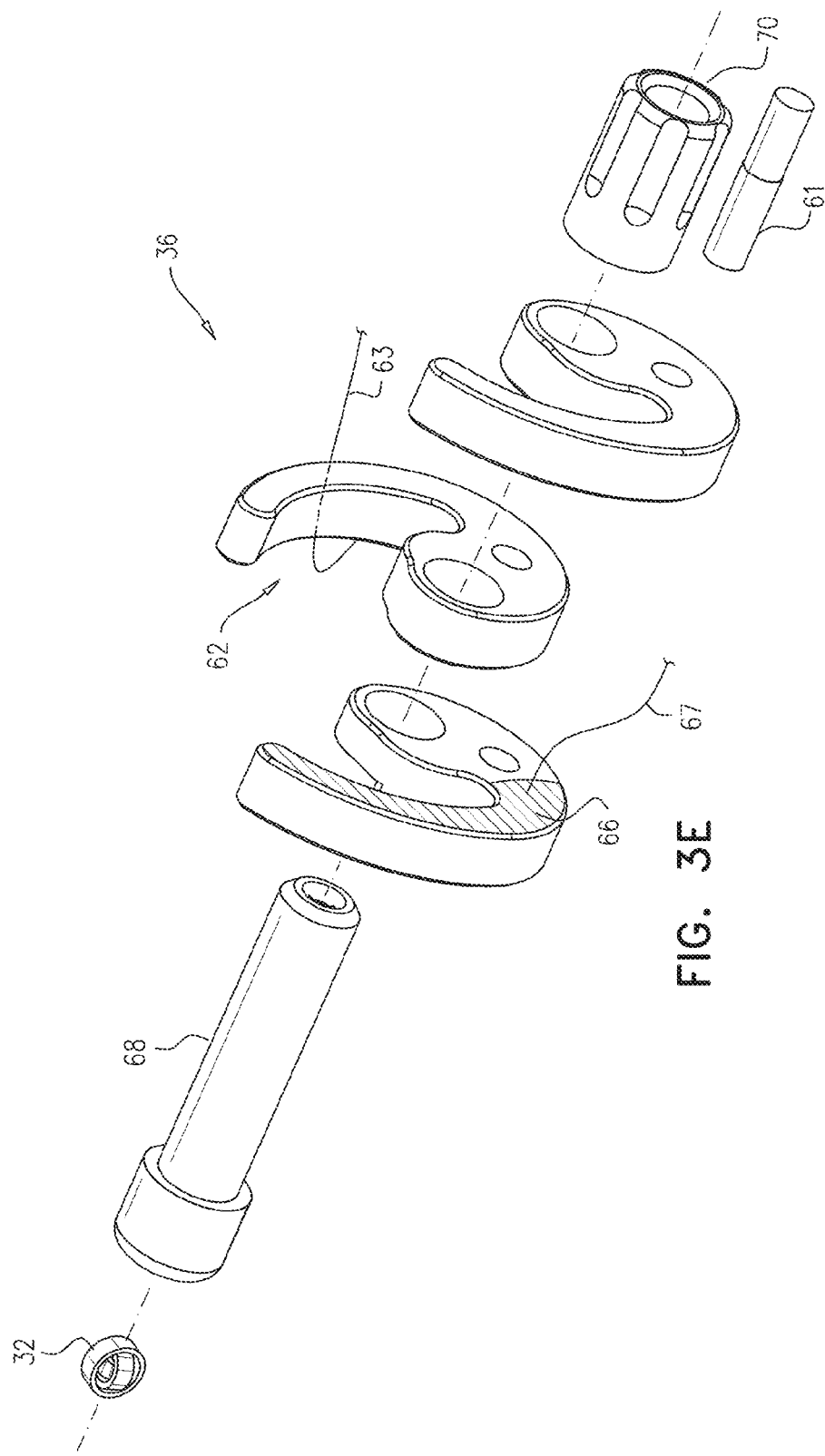

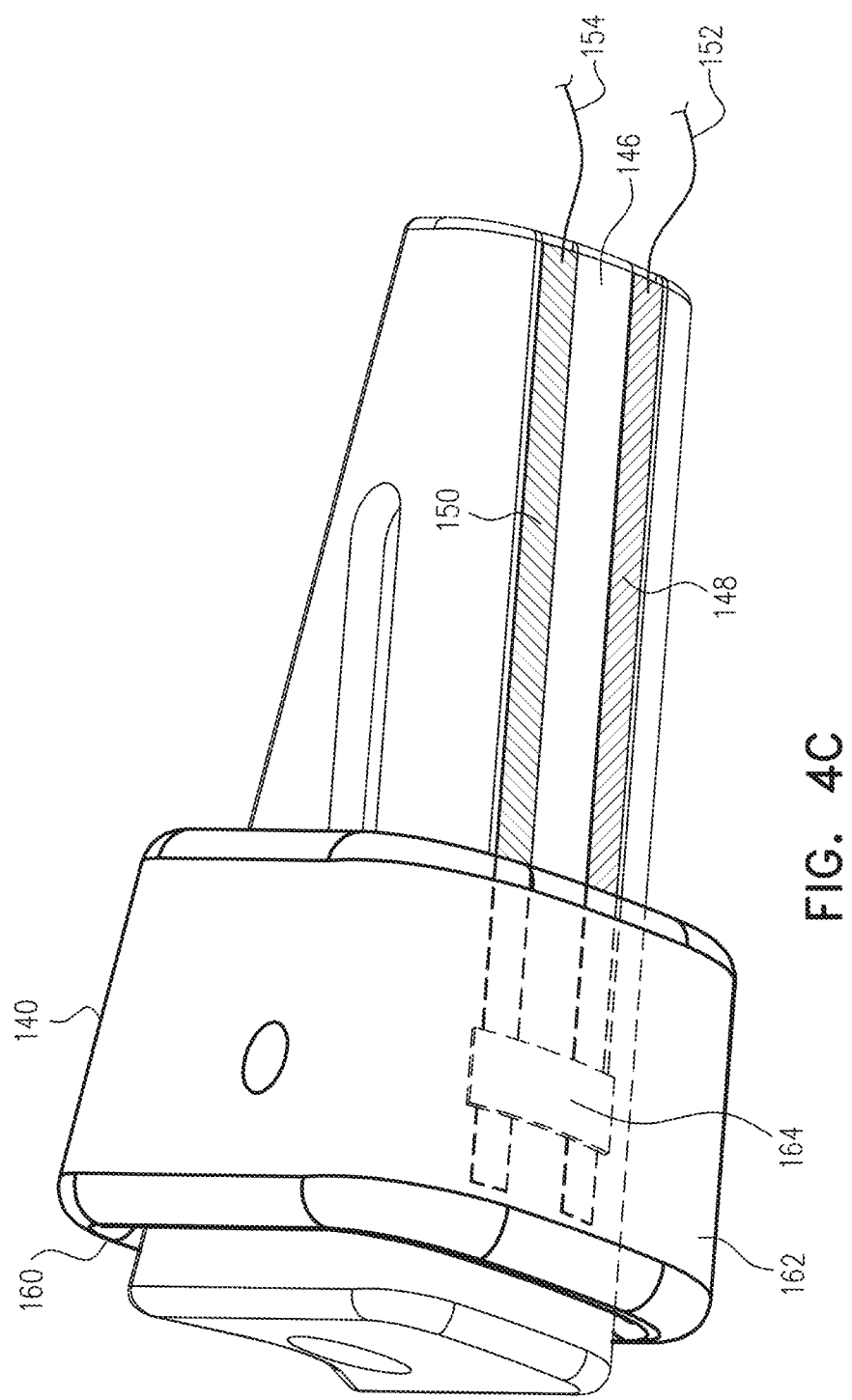

ADJUSTABLE TRACKING SENSOR SUITABLE FOR DIFFERENT RIGID TOOLS

FIELD OF THE INVENTION

This invention relates generally to tracking of tools, and specifically to improving the tracking of a rigid tool used in surgery.

BACKGROUND OF THE INVENTION

In a surgical procedure the distal end of a rigid tool used in the procedure, such as an endoscope, may be tracked by fixedly incorporating a location sensor in the tool. A typical surgical procedure where such a tool is used comprises an investigative ENT (Ear, Nose and Throat) procedure. The incorporated sensor may be located at the distal end of the tool; alternatively, the incorporated sensor may be located away from the distal end, towards the proximal end of the tool. In the latter case, since the incorporated sensor is in a fixed position, compensation for the displacement of the sensor from the distal end may be applied to the sensor's measured location.

SUMMARY OF THE INVENTION

An embodiment of the present invention provides apparatus, including:

a rigid gripper configured to fasten around a cylindrical object;

a pair of conductors attached to the gripper so as to make contact with one another, while the gripper is fastened around the cylindrical object, at a location along a length of the conductors that varies responsively to a diameter of the cylindrical object; and a sensing circuit configured to measure an impedance of a current passing through the pair of conductors and to generate an indication of the diameter responsively to the impedance.

In a disclosed embodiment the rigid gripper includes a pair of jaws rotating about a common hinge so as to fasten around the cylindrical object, and each of the conductors is attached to a respective jaw.

In a further disclosed embodiment the apparatus includes a sensor, fixedly attached to the rigid gripper, configured to generate a sensor signal indicative of a location of the gripper.

In a yet further disclosed embodiment the rigid gripper includes a wedge configured to slide into an open rectangular frame so as to fasten about the cylindrical object, and the pair of conductors includes a first conductor attached to the frame, and a second conductor attached to the wedge. Typically the second conductor includes a pair of parallel conducting lines, and the first conductor connects the parallel conducting lines.

There is further provided, according to an embodiment of the present invention apparatus, including:

a rigid cylindrical probe having a distal end;

a rigid gripper configured to fasten around the cylindrical probe;

a sensor, fixedly attached to the rigid gripper, configured to generate a sensor signal indicative of a location of the gripper;

a pair of conductors attached to the gripper so as to make contact with one another, while the gripper is fastened around the cylindrical probe, at a location along a length of the conductors that varies responsively to a diameter of the cylindrical endoscope; and a processor configured to:

measure an impedance of a current passing through the pair of conductors, generate an indication of the diameter responsively to the impedance, and formulate a metric of a location of the distal end responsively to the indication of the diameter and the sensor signal.

The processor may be configured to generate an indication of a displacement of the sensor to the probe responsively to the impedance, and formulate the metric of the location of the distal end responsively to the indication of the displacement.

There is further provided, according to an embodiment of the present invention, a method, including:

receiving a computerized tomography scan of a patient;

registering an image of the patient derived from the scan with a magnetic tracking system configured to track a sensor in proximity to the patient;

fixing the sensor to a rigid gripper configured to fasten around a cylindrical probe having a distal end;

attaching a pair of conductors to the gripper so as to make contact with one another, while the gripper is fastened around the cylindrical probe, at a location along a length of the conductors that varies responsively to a diameter of the cylindrical probe;

measuring an impedance of a current passing through the pair of conductors and generating an indication of the diameter responsively to the impedance;

positioning the distal end in contact with the patient;

while the distal end is in contact with the patient, determining, responsively to the indication of the diameter, a vector representing a translation from the sensor to the distal end; and while tracking the sensor with the magnetic tracking system, adding the vector to a location of the sensor to determine a position of the distal end.

In an alternative embodiment the method includes determining a displacement from the sensor to the cylindrical probe responsively to the impedance, and determining the vector responsively to the displacement.

In a further alternative embodiment the method includes determining a displacement from a point of contact of the distal end with the patient, along an axis of the cylindrical probe, to a region on the axis in proximity to the sensor, and determining the vector responsively to the displacement.

There is further provided, according to an embodiment of the present invention, a method, including:

fastening a rigid gripper around a cylindrical object;

attaching a pair of conductors to the gripper so as to make contact with one another, while the gripper is fastened around the cylindrical object, at a location along a length of the conductors that varies responsively to a diameter of the cylindrical object; and measuring an impedance of a current passing through the pair of conductors and generating an indication of the diameter responsively to the impedance.

There is further provided, according to an embodiment of the present invention, a method, including:

providing a rigid cylindrical probe having a distal end;

fastening a rigid gripper around the cylindrical probe;

fixedly attaching a sensor to the rigid gripper, wherein the sensor is configured to generate a sensor signal indicative of a location of the gripper;

attaching a pair of conductors to the gripper so as to make contact with one another, while the gripper is fastened around the cylindrical probe, at a location along a length of the conductors that varies responsively to a diameter of the cylindrical endoscope;

measuring an impedance of a current passing through the pair of conductors;

generating an indication of the diameter responsively to the impedance; and formulating a metric of a location of the distal end responsively to the indication of the diameter and the sensor signal.

There is further provided, according to an embodiment of the present invention, apparatus, including:

a cylindrical probe having a distal end;

a rigid gripper configured to fasten around the cylindrical probe;

a sensor, fixed to the rigid gripper, and configured to be tracked by a magnetic tracking system;

a pair of conductors attached to the gripper so as to make contact with one another, while the gripper is fastened around the cylindrical probe, at a location along a length of the conductors that varies responsively to a diameter of the cylindrical probe; and a processor configured to:

receive a computerized tomography scan of a patient, register an image of the patient derived from the scan with the magnetic tracking system, measure an impedance of a current passing through the pair of conductors and generate an indication of the diameter responsively to the impedance, while the distal end is in contact with the patient, determine, responsively to the indication of the diameter, a vector representing a translation from the sensor to the distal end, and while tracking the sensor with the magnetic tracking system, add the vector to a location of the sensor to determine a position of the distal end.

The present disclosure will be more fully understood from the following detailed description of the embodiments thereof, taken together with the drawings, in which:

BRIEF DESCRIPTION OF THE DRAWINGS

FIGS. 3A-3E are different views of a gripper used in the system, according to an embodiment of the present invention;

FIGS. 4A-4C are different views of a gripper used in the system, according to an alternative embodiment of the present invention;

DETAILED DESCRIPTION OF EMBODIMENTS

Overview

A number of rigid tools used in surgery do not have location sensors fixedly incorporated into the tool, and while such tools may be tracked by other means, such as fluoroscopy, this type of tracking is typically more inconvenient than tracking using a location sensor on the tool.

Embodiments of the present invention overcome the problem associated with tools that do not have sensors incorporated in the tools, by providing a sensor that is attached to the tool at any convenient position on the tool. Once attached, the displacement of the attached sensor from the distal end of the tool is automatically measured, and is incorporated into the readings of the attached sensor.

In one embodiment, a rigid gripper is fastened around a cylindrical object, assumed by way of example to be a surgical tool, and a pair of conductors are attached to the gripper so as to make contact with one another, while the gripper is fastened around the tool. The contact is at a location along a length of the conductors that varies responsively to a diameter of the tool.

A sensing circuit measures an impedance of a current passing through the pair of conductors and generates an indication of the diameter responsively to the impedance. A location sensor may be attached to the gripper, and knowing the diameter of the tool, a displacement of the sensor relative to the tool may be evaluated and the displacement may be used in tracking the tool.

In an alternative embodiment a computerized tomography scan of a patient is received, and an image of the patient derived from the scan is registered with a magnetic tracking system configured to track a sensor in proximity to the patient.

The sensor may be fixed to a rigid gripper configured to fasten around a cylindrical probe having a distal end. A pair of conductors may be attached to the gripper so as to make contact with one another, while the gripper is fastened around the cylindrical probe, at a location along a length of the conductors that varies responsively to a diameter of the cylindrical probe.

An impedance of a current passing through the pair of conductors may be measured and an indication of the diameter may be generated responsively to the impedance.

The distal end may be positioned in contact with the patient, and while so positioned, a vector representing a translation from the sensor to the distal end may be determined responsively to the diameter.

While tracking the sensor with the magnetic tracking system, the vector may be added to a location of the sensor to determine a position of the distal end.

System Description

Figure 1:
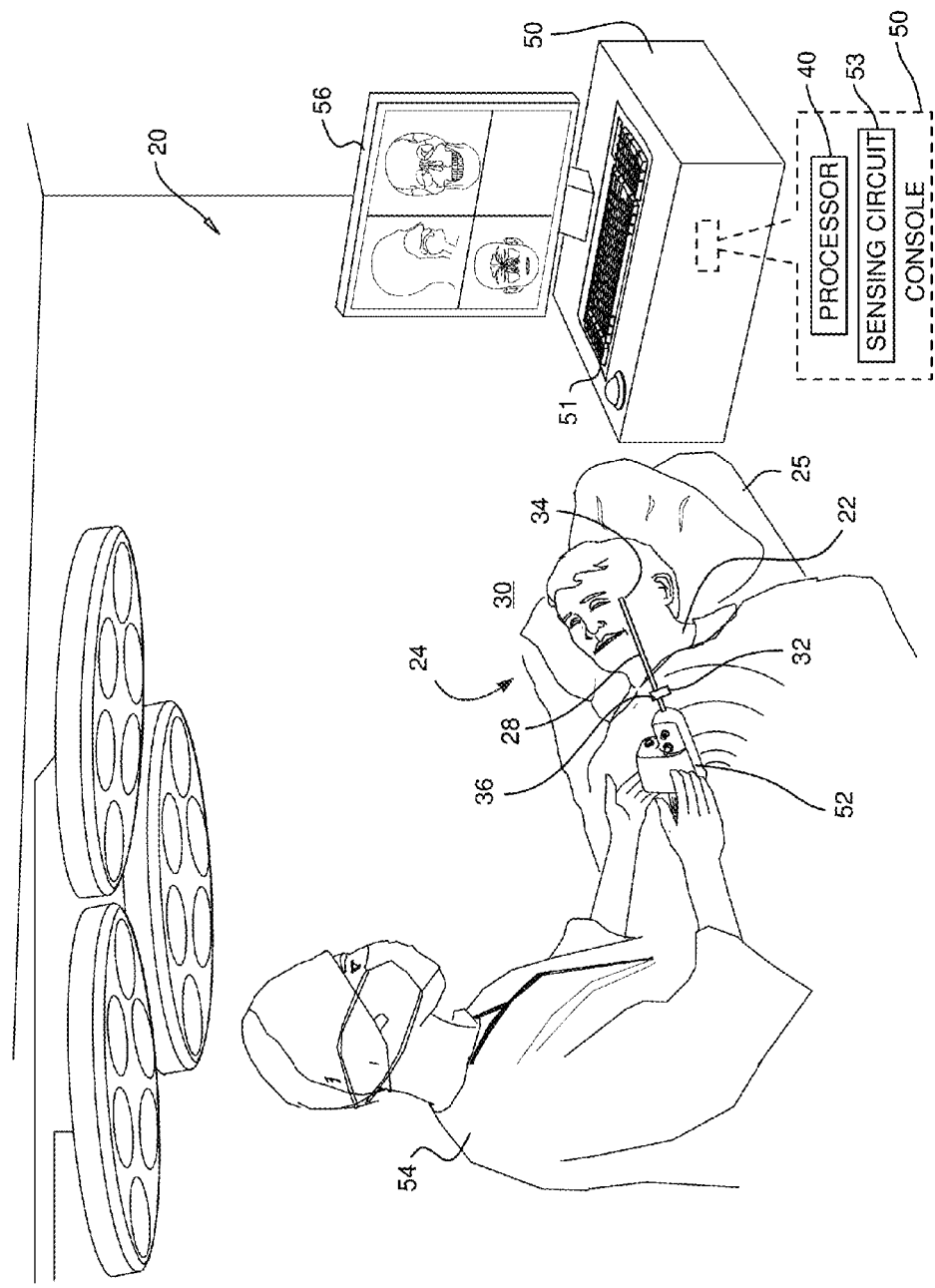
FIG. 1 is a schematic illustration of a nasal sinus surgery system, according to an embodiment of the present invention.
Figure 2:
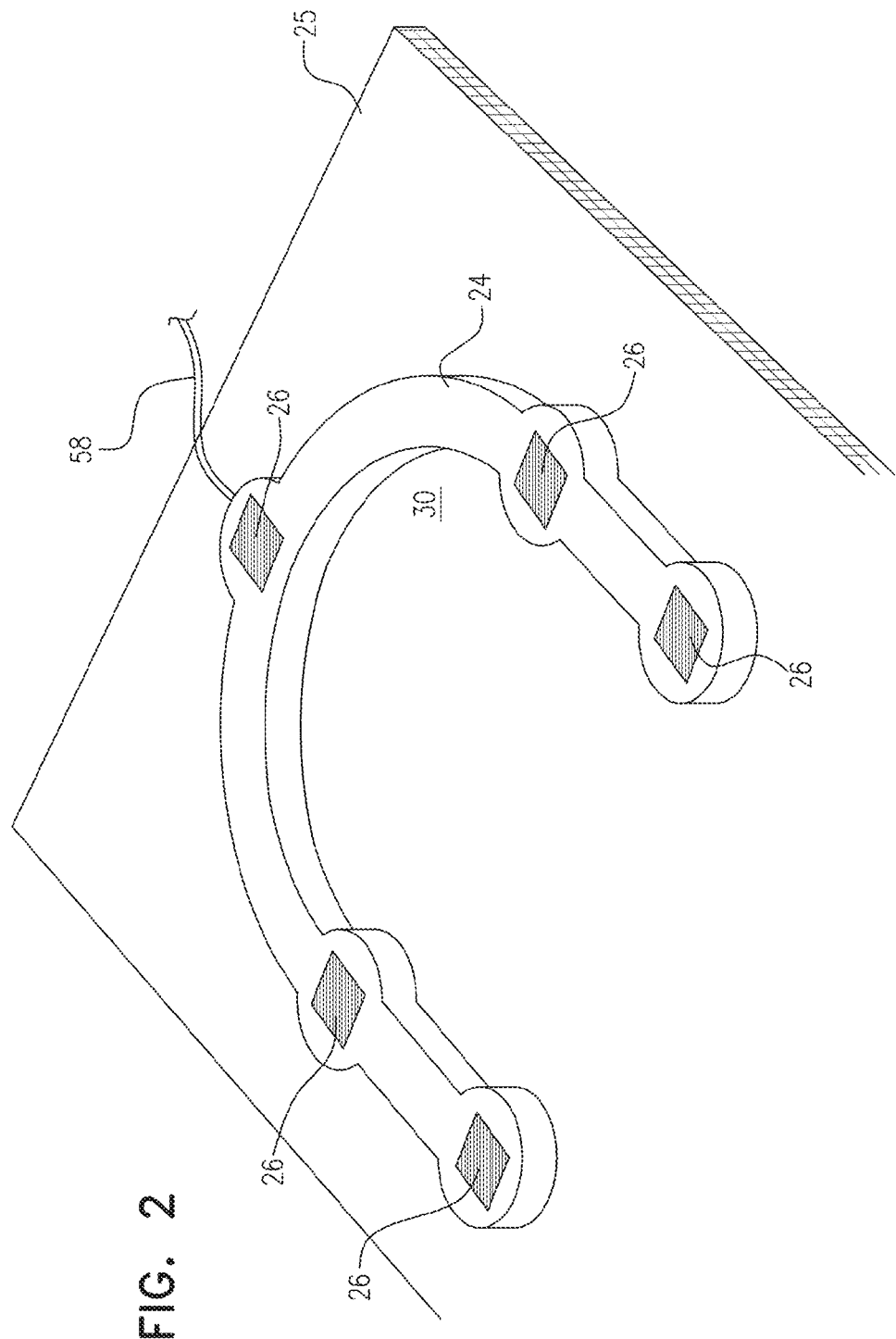
FIG. 2 is a schematic illustration of a magnetic field radiation assembly used in the surgery system, according to an embodiment of the present invention.

Reference is now made to FIG. 1, which is a schematic illustration of a nasal sinus surgery system 20, and to FIG. 2, which is a schematic illustration of a magnetic field radiation assembly 24 used in the system, according to an embodiment of the present invention. System 20 is typically used during an invasive and/or investigative procedure on a nasal sinus of a patient 22.

For the procedure, assembly 24 may be positioned beneath the head of the patient, for example by fixing the assembly to a bed 25 upon which the patient is lying, and the patient's head may be clamped so that it does not move relative to the assembly. Assembly 24 comprises five magnetic field radiators 26, which by way of example are fixed in a horseshoe shaped frame, the frame being positioned beneath the patient so that the radiators surround the head of patient 22. Radiators 26 are configured to radiate alternating magnetic fields into a region 30, in proximity to assembly 24 and which includes the head of patient 22. The alternating magnetic fields induce signals in a sensor 32, typically a set of three orthogonal coils, and the signals may be analyzed to derive the location and orientation of the sensor with respect to assembly 24. It will be understood that the location and orientation of sensor 32 may be determined for substantially any positioning of the sensor within region 30.

As is described in more detail below, sensor 32 is affixed to a rigid sensor holder 36, which fastens around a rigid cylindrical probe 28, so that the holder grips the probe. Sensor holder 36 is also referred to herein as rigid gripper 36, or just as gripper 36. Determination of the location and orientation of the sensor enables the location and orientation of a distal end 34 of the probe, that may be inserted into the nasal sinus of the patient, to be tracked. Gripper 36 is configured to connect to rigid probes 28 having different diameters and the probes with different diameters are differentiated in the description herein, as necessary, by appending a letter to the identifying numeral 28.

A system using magnetic field radiators, such as radiators 26, for tracking an entity inserted into a patient is described in U.S. patent application Ser. No. 14/792,823, to Govari et al., which is incorporated herein by reference. In addition, the Carto® system produced by Biosense Webster, of Diamond Bar, Calif., uses a tracking system similar to that described herein for finding the location and orientation of a coil in a region irradiated by magnetic fields.

Elements of system 20, including radiators 26, may be controlled by a system processor 40, comprising a processing unit communicating with one or more memories. Typically the elements may be connected by cables to the processor, for example, radiators 26 may be connected by a cable 58 to processor 40. Alternatively or additionally, the elements may be coupled wirelessly to the processor. Processor 40 may be mounted in a console 50, which comprises operating controls 51 that typically include a keypad and/or a pointing device such as a mouse or trackball. Console 50 also connects to other elements of system 20, such as proximal end 52 of probe 28. A physician 54 uses the operating controls to interact with the processor while performing the procedure, and the processor may present results produced by system 20 on a screen 56.

For clarity, conducting leads from gripper 36, typically to a proximal end 52 of probe 28, are not shown in FIG. 1, but are shown in other figures. A sensing circuit 53 may be incorporated into console 50, the circuit coupling to the conducting leads of gripper 36, and being configured to measure an impedance between the leads. Further details of the functionality of circuit 53 are provided below. In some embodiments, rather than circuit 53 being located in console 50, the circuit is incorporated into gripper 36. Such incorporation enables the gripper to act as a stand-alone unit.

Processor 40 uses software stored in a memory of the processor to operate system 20. The software may be downloaded to processor 40 in electronic form, over a network, for example, or it may, alternatively or additionally, be provided and/or stored on non-transitory tangible media, such as magnetic, optical, or electronic memory.

Figure 3D:
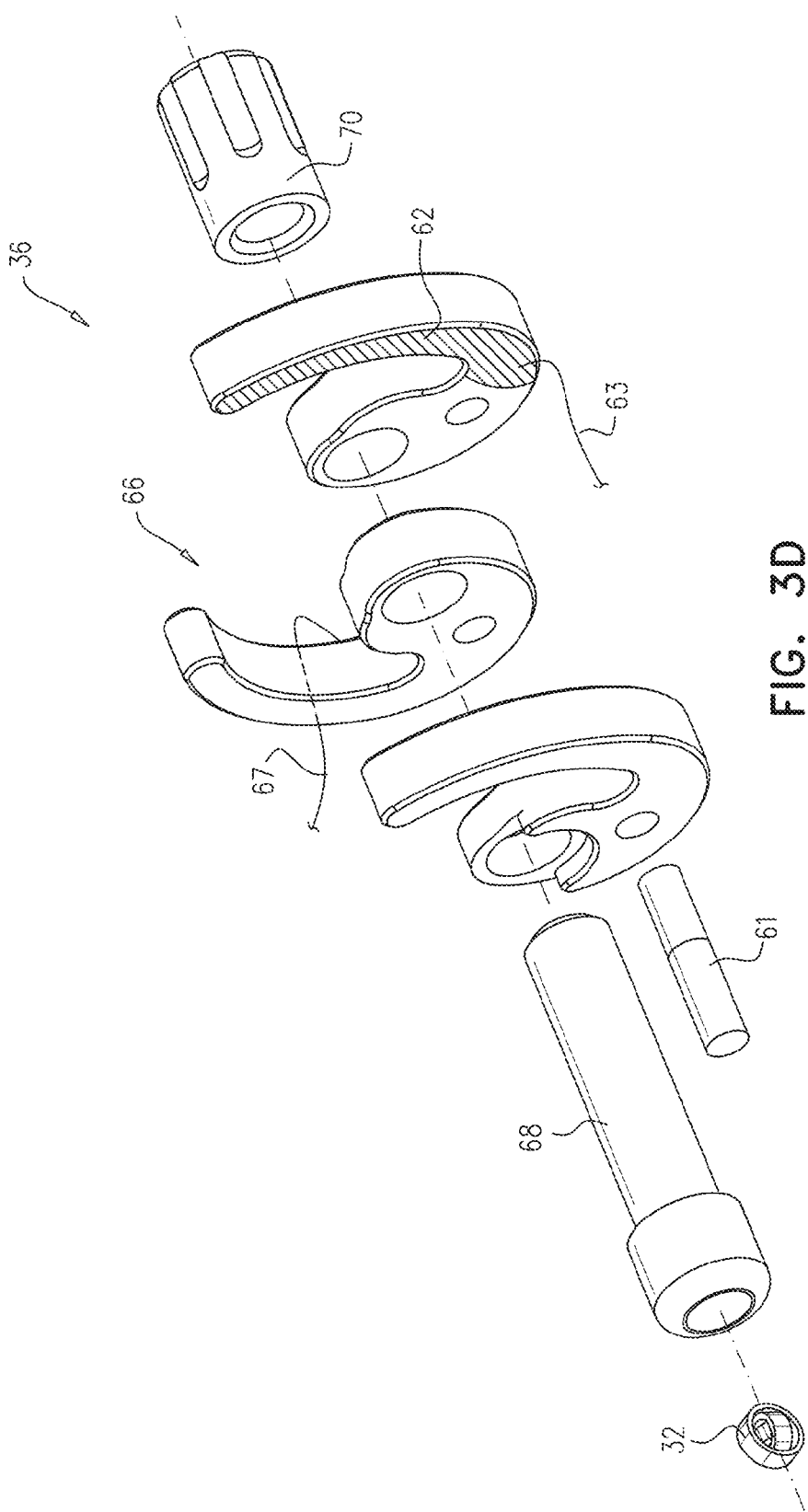

FIG. 3A is a schematic perspective view of gripper 36, FIG. 3B is a schematic perspective view of the gripper fastened around a portion of a rigid probe 28A, FIG. 3C is a schematic perspective view of the gripper fastened around a portion of a rigid probe 28B, and FIGS. 3D and 3E are schematic exploded views of the gripper, according to an embodiment of the present invention. As shown in FIGS. 3A, 3D and 3E, gripper 36 comprises a curved double-jawed section 60 connected by a rod 61, one of the jaws of section 60 having a plane conducting surface 62 with a lead 63 connecting to the surface. Gripper 36 also comprises a curved single-jawed section 64 having a plane conducting surface 66 with a lead 67 connecting to the surface.

Sections 60 and 64 are both able to rotate about a rod 68, which acts as a hinge for the sections and which at its distal end has sensor 32 fixed to the rod, and at its proximal end is configured to accept a locking screw 70. Tightening of the locking screw fixes sensor 32 to gripper 36. In addition, when sections 60 and 64 rotate towards each other, conducting surfaces 62 and 66 contact each other galvanically. As stated above, leads 63 and 67 may be coupled to sensing circuit 53, enabling processor 40 to record an impedance between the two contacting surfaces.

FIG. 3B illustrates gripper 36 after it has been configured to fasten around a portion of rigid probe 28A, i.e., by sections 60 and 64 being rotated to grip the probe, after which locking screw 70 may be tightened to maintain the gripper rigidly attached to the probe. In this case, because of the relatively large diameter of probe 28A, there is a relatively small area of contact between surfaces 62 and 66, so that a measured impedance between the two surfaces is large.

FIG. 3C illustrates gripper 36 after it has been configured to fasten around a portion of rigid probe 28B, which has a smaller diameter than probe 28A. Because of the smaller diameter of probe 28B, once the gripper has been tightened in place onto the probe, there is a relatively large area of contact between surfaces 62 and 66, so that a measured impedance between the two surfaces is small.

Figure 5:
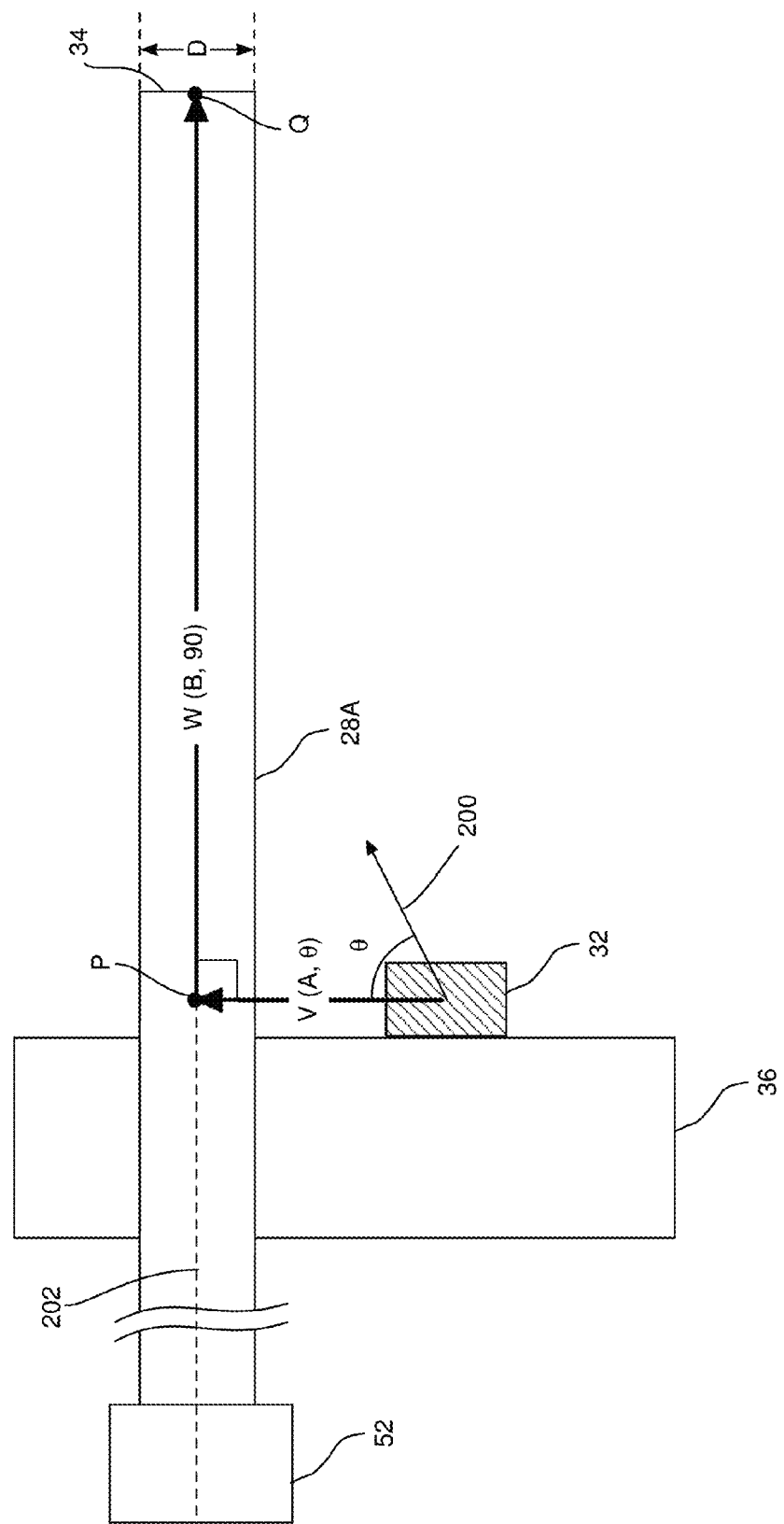
FIG. 5 is a schematic diagram illustrating vectors associated the gripper of FIGS. 3A-3E, according to an embodiment of the present invention.

Typically, a distance A of an axis of symmetry of the rigid probe to sensor 32 depends on a diameter D of the probe. In some embodiments, the jaws of sections 60 and 64 are shaped so that after they grip probe 28, distance A is substantially the same for different diameters D of the probe. The axis of symmetry, diameter D, and distance A are illustrated in FIG. 5.

In embodiments of the present invention processor 40 uses sensing circuit 53 to perform a calibration that measures an impedance Z of contacting surfaces 62 and 64, and that generates a correspondence between diameter D, distance A, and impedance Z. In some embodiments, impedance Z is measured by passing a low frequency or DC current through contacting surfaces 62 and 64, so that the measured impedance is effectively an ohmic resistance of the contacting surfaces.

Typically, gripper 36 is able to accept rigid probes 28 having diameters in a range of 1 mm-10 mm, although in some embodiments rigid probes with diameters outside this range may be accepted by holder 36.

Figure 4A:
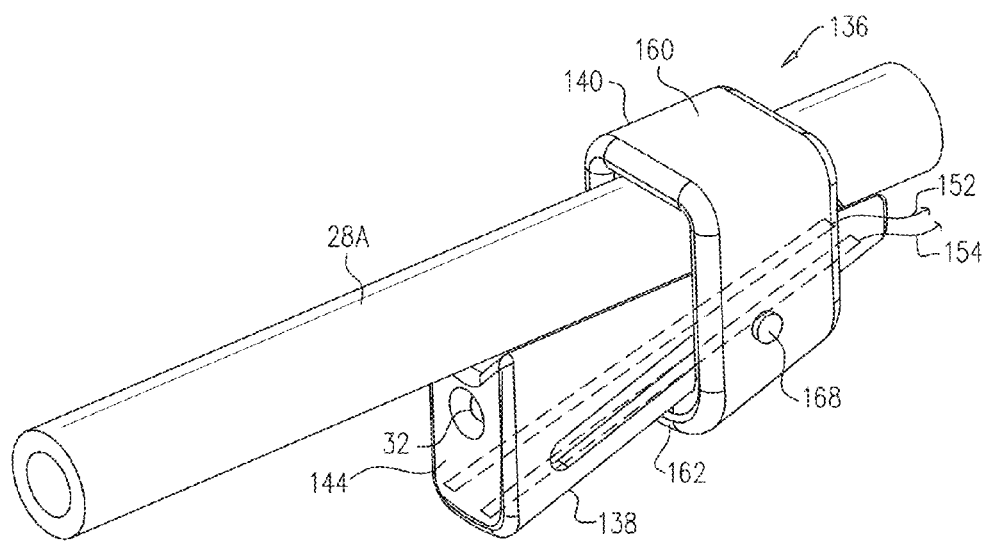
Figure 4B:
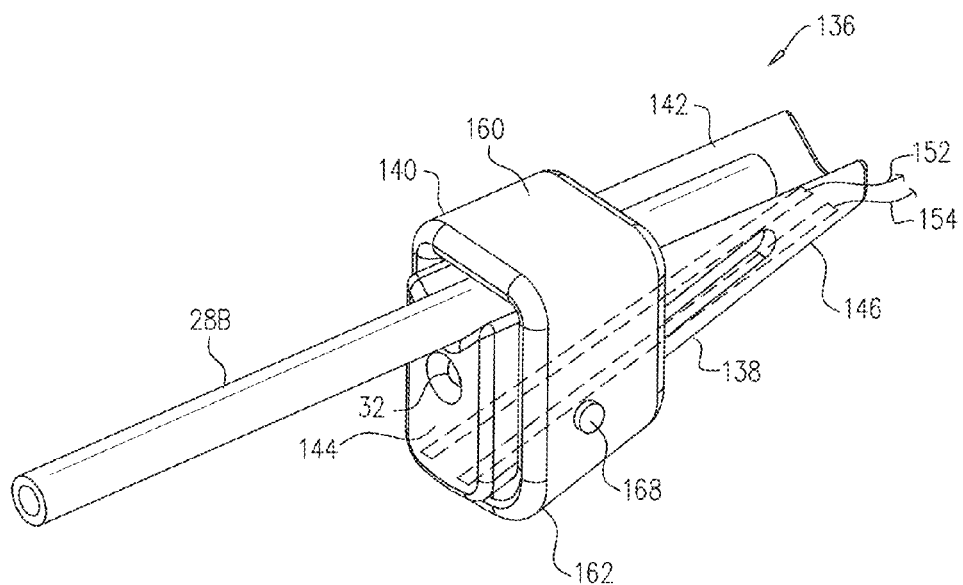

FIG. 4A is a schematic perspective view of a sensor holder 136 fastening around a portion of rigid probe 28A, FIG. 4B is a schematic perspective view of sensor holder 136 fastening around a portion of rigid probe 28B, and FIG. 4C is a schematic perspective view of the holder from an alternative viewpoint to that of FIGS. 4A and 4B, according to an alternative embodiment of the present invention.

While sensor holder 136 is physically different from sensor holder 36, it performs similar functions, e.g., fastening around cylindrical probes of different diameters while fixedly gripping sensor 32. Thus, in embodiments of the present invention, sensor holder 136 may be used instead of sensor holder 36, so that the description of the operation of sensor 36 (FIGS. 3A-3E) applies, mutatis mutandis, to the operation of sensor holder 136. Sensor holder 136 is also referred to herein as gripper 136.

Gripper 136 comprises a wedge 138, which mates with an open, generally rectangular frame 140, by sliding into frame 140. Wedge 138 has a V-shaped upper surface 142 which is dimensioned to accept rigid probes 28 having diameters typically in a range of 1 mm-10 mm, and sensor 32 is fixed into a distal face 144 of the section. Wedge 138 has a lower surface 146 which is not parallel to upper surface 142, the upper and lower surfaces thus forming wedge 138. Incorporated into lower surface 146 are two conducting lines 148, 150, and there are respective conducting leads 152, 154 from the conducting lines.

Rectangular frame 140 has an upper surface 160 which is parallel to V-shaped surface 142, and a lower surface 162 which is parallel to lower surface 146. As shown in FIG. 4C, lower surface 162 also comprises a conductor 164 which connects conducting lines 148 and 150 when wedge 138 slides into the rectangular frame to grip a rigid probe.

FIG. 4A and FIG. 4B respectively illustrate gripper 136 fastening around a portion of rigid probe 28A and a portion of rigid probe 28B. In both cases, the rigid probe is gripped by upper surface 160 of the rectangular frame and by the V-shaped surface of the wedge. Once the rigid probe has been gripped, a locking screw 168 may be tightened to maintain the holder rigidly attached to the probe.

As stated above, conductor 164 connects conducting lines 148 and 150. As is apparent from FIGS. 4A and 4B, when gripper 136 fastens around probe 28A, the overall length of the connected conducting lines is larger than the overall length of the connected lines when the gripper fastens around probe 28B. Thus, the impedance of the connected conducting lines, measured by sensing circuit 53 between conducting leads 152, 154, when probe 28A is gripped is larger than when probe 28B is gripped.

In embodiments of the present invention processor 40 uses sensing circuit 53 to perform a calibration that generates a correspondence between an impedance Z of connected conducting lines 148, 150, a diameter D of the rigid probe, and a distance A of an axis of symmetry of the rigid probe to sensor 32.

FIG. 5 is a schematic diagram illustrating vectors associated with gripper 36 when it fastens around rigid probe 28A, according to an embodiment of the present invention. As explained above, once gripper 36 is fastened to grip probe 28A, sensor 32 is fixed to the gripper. Signals from the sensor, generated in response to the magnetic fields from radiators 26 interacting with the sensor, are used to determine a location and an orientation of the sensor with respect to a frame of reference defined by the radiators. Conducting wires which convey the signals from the sensor may be connected to proximal end 52 of probe 28A, and from there to console 50. The conducting wires are not shown in FIG. 5.

The sensor is assumed to have a sensor direction 200, typically, but not necessarily, the direction of an internal axis of symmetry of the sensor, and the orientation referred to herein measures the orientation of the sensor direction with respect to a frame of reference defined by radiators 26. Probe 28A is assumed to have an axis of symmetry 202.

Sensor direction 200 of sensor 32 is shown schematically in FIG. 5 as an arrow. In addition, by virtue of being fixed to gripper 36, sensor 32 has a known orientation θ with respect to sensor direction 70 that is 90°, i.e., orthogonal, to axis of symmetry 202. There is thus a known displacement vector (A, θ), herein also termed vector V, corresponding to a translation from sensor 32 to a point P on axis 202, as shown in FIG. 5.

As is stated above, the distance A from sensor 32 to the axis of symmetry typically depends on the diameter D of probe 28A. Once the calibration referred to above, between the impedance Z of contacting surfaces 62, 64, diameter D, and distance A has been performed, processor 40 is able to calculate the diameter D and distance A for probe 28A from the measured impedance Z of the contacting surfaces.

The distance from point P, measured along axis of symmetry 202, to distal end 34, also referred to as point Q is assumed to be a distance B. While the direction of Q, at 90° to vector V and along axis 202, is known, unlike distance A, distance B (PQ) is not known when gripper 36 is fastened to probe 28A. However, as is described below, in operation of system 20 processor 40 is able to calculate distance B.

Figure 6:
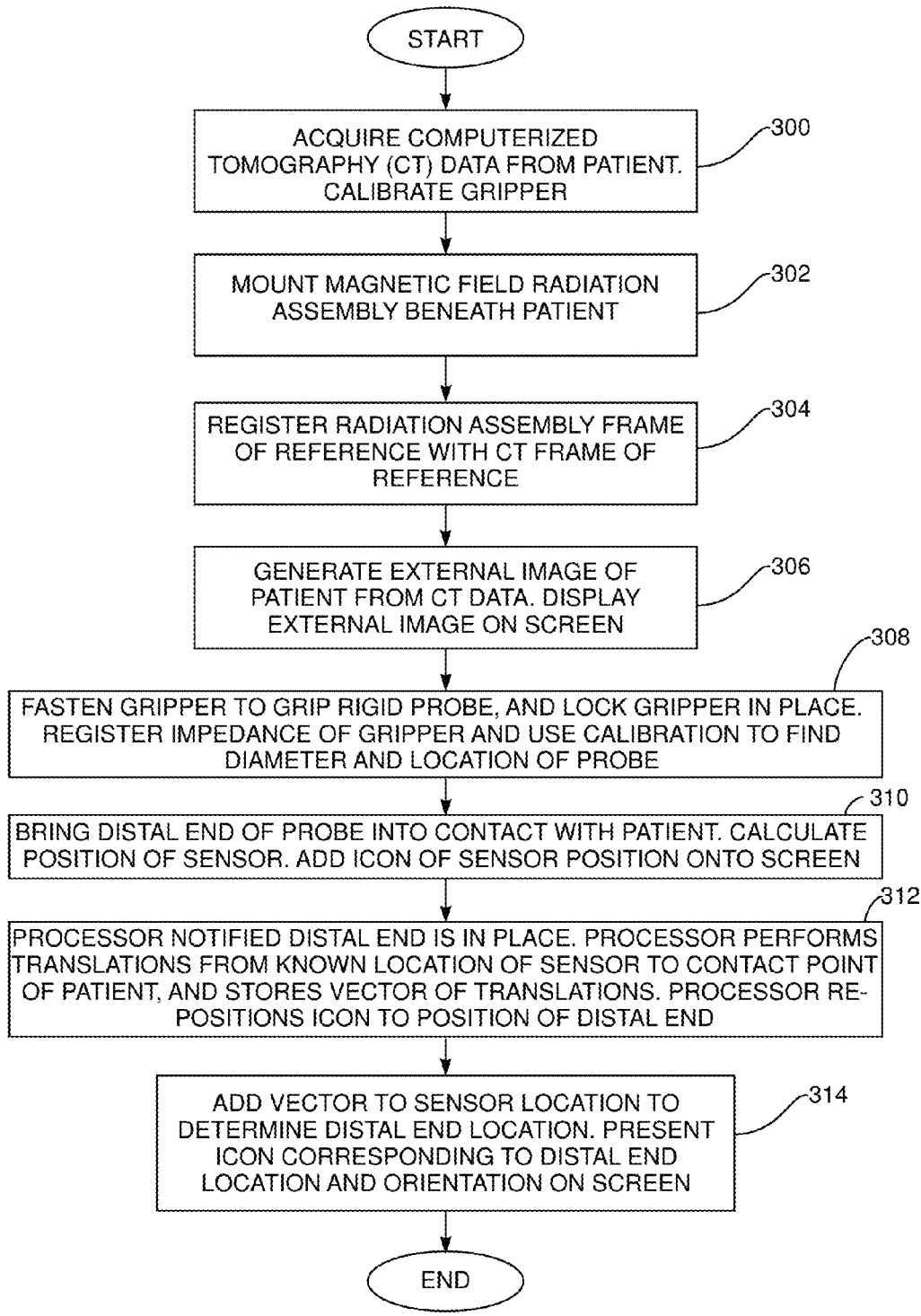
FIG. 6 is a flowchart of steps that are implemented in the operation of the system, according to an embodiment of the present invention.
Figure 7:
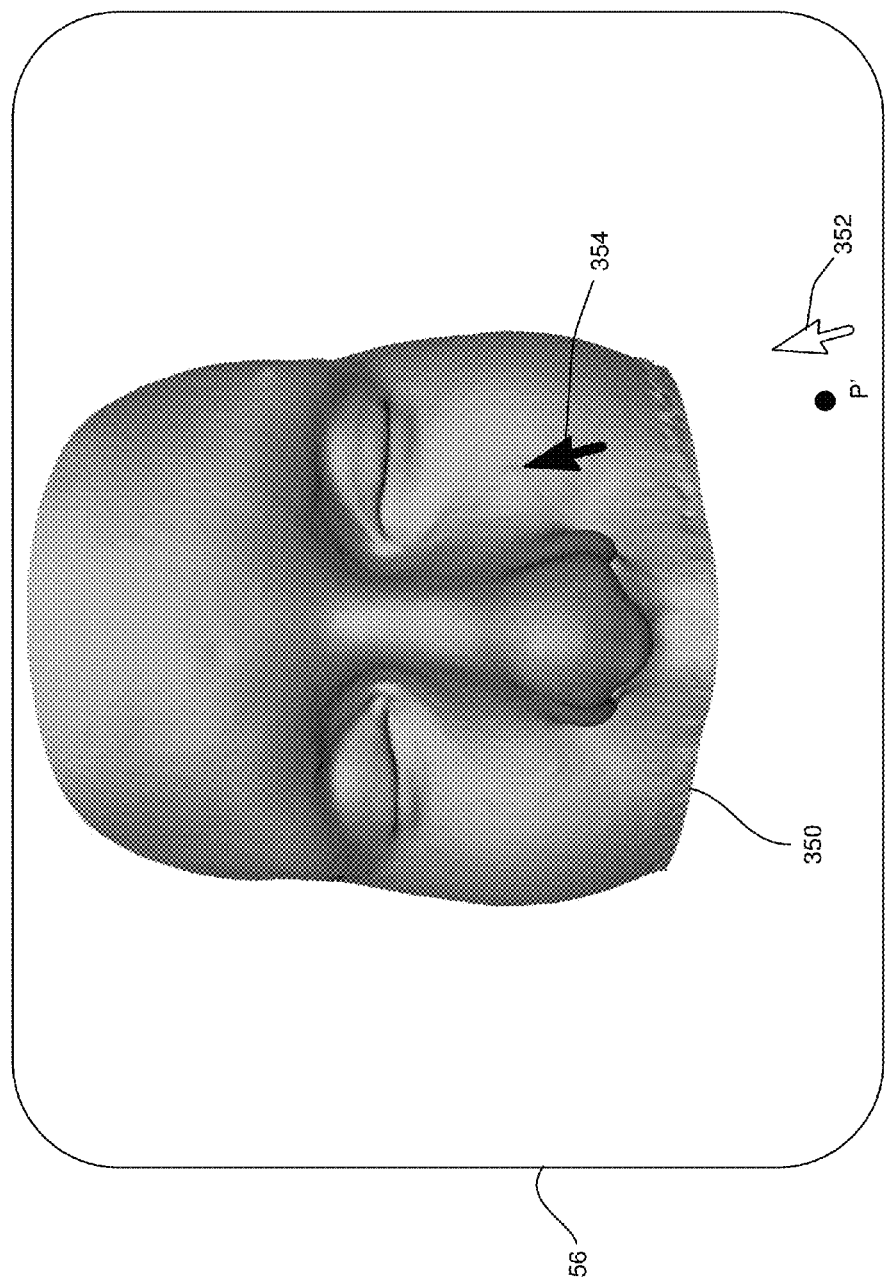
FIG. 7 is a schematic illustration of a screen during implementation of the flowchart, according to an embodiment of the present invention.

FIG. 6 is a flowchart of steps that are implemented in the operation of system 20, and FIG. 7 is a schematic illustration of screen 56 during implementation of the flowchart, according to an embodiment of the present invention. For clarity, the flowchart is described assuming gripper 36 (FIGS. 3A-3E) fastens around rigid probe 28A, where the jaws of the gripper are not shaped so that distance A is the same for different diameters of gripped probes. Those having ordinary skill in the art will be able to adapt the description, mutatis mutandis, for embodiments where the jaws are shaped so that distance A is the same, and also where gripper 136 is used in place of gripper 36.

In an initial step 300, the head of patient 22 is scanned by computerized tomography (CT), herein by way of example assumed to be fluoroscopic CT, and the CT data from the scan is acquired by processor 40. The CT scan of patient 22 may be performed independently of the implementation of the remaining steps of the flowchart, which correspond to the sinus surgery procedure.

In addition, processor 40 performs the calibration described above for sensor holder 36, the calibration generating a correspondence between diameter D, distance A, and impedance Z.

Typically, step 300 may be performed a number of days before the following surgery steps of the procedure.

In a first procedure step 302, radiation assembly 24 is mounted beneath the head of patient 22. Radiators 26 are then operated, and in a registration step 304 a frame of reference of the radiators is registered with the frame of reference of the subject's head. The registration is typically by any means known in the art, e.g., by placing a magnetic field sensor coil, or a grouping of such coils, in one or more known locations and orientations with respect to the external features of the patient as well as with the frame holding the radiators.

In an initial display step 306, processor 40 generates a representation 350, also referred to herein as image 350, of external features of the patient, using the CT data received in step 300. The CT data is in the form of voxels with Hounsfield units (HU), and it will be appreciated that image 350 of the external features of patient 22 can be generated from voxel values and their HU values. Processor 40 displays image 350 on screen 56, and FIG. 7 schematically illustrates the image as displayed on the screen.

In an operation step 308, physician 54 fastens gripper 36 to probe 28A, and locks the gripper into place. Processor 40 uses sensing circuit 53 to read the impedance generated by the pair of contacting conducting surfaces 62 and 66. Using the calibration acquired in step 300, and from the measured value of the impedance the processor calculates a value of the diameter D for probe 28A, and a value of the distance A.

Once the gripper is locked in place, in a continuing operation step 310 the physician brings distal end 34 of the probe into contact with a selected region of the external features of the patient, for example a region at the side of the patient's nose.

The positioning of the distal end of necessity brings gripper 36 and its encapsulated sensor 32 into region 30 (FIGS. 1 and 2), so that processor 40 is able to calculate the location and orientation of the sensor. Once the processor has performed this calculation, it typically introduces an icon 352, representative of sensor direction 70, onto screen 56, in proximity to image 350. Icon 352 is located and oriented on screen 56 in accordance with the location and orientation of sensor 32, determined from the sensor signals, within the common frame of reference of image 350 and radiators 26.

By virtue of the fact that the physician is holding probe 28, the physician is aware of the actual location and orientation of sensor 32. Comparison of the location and orientation of icon 352 with the actual location and orientation of sensor 32 provides confirmation to the physician of the correct operation of system 20.

In a probe calibration step 312 the physician notifies processor 40 that the distal end of the probe is in contact with an external feature of the patient, typically by using controls 51. On receipt of the notification, the processor performs two translations on the known location of sensor 32. A first translation corresponds to vector V (A, θ), (FIG. 5) so that the processor translates the location of the sensor by a value A along a direction defined by θ to a point P on axis 202 (FIG. 5). A point P', corresponding to point P, is drawn in FIG. 7, to illustrate the termination of the first translation. Typically, point P' is not drawn on screen 56.

From point P the processor performs a second translation, in a direction along axis 202. The processor uses the data for image 350 to determine the actual length of the second translation, by determining from the image data where point P, moving along axis 202, meets an external surface of patient 22. The meeting with the external surface occurs when there is a change in value of the Hounsfield units of the image data, and the meeting is assumed to be at point Q on axis 202. Q is a distance B, now known, from point P, and the second translation thus corresponds to a displacement vector W (B, 90), illustrated in FIG. 5.

It will be understood that even though the calculation of the position of point Q uses CT image data, since the image is registered with the actual external features of patient 22, point Q corresponds with an actual external point of the patient.

At the conclusion of the calibration step the processor deletes icon 352 from screen 56, and positions an icon 354 at a position of image 350 corresponding to point Q. Comparison of the location and orientation of icon 354 with the actual location and orientation of distal end 34 provides confirmation to the physician of the correct completion of the calibration step. Typically, processor 40 sizes icon 354 according to the diameter D determined in step 308.

The sum of the two translations, V+W, of the calibration step is a vector that is stored by processor 40.

In a continuing tracking step 314, the processor adds the vector stored in step 312 to the location of the sensor in order to determine the location of distal end 34. The orientation of the distal end corresponds to the direction of axis 202, which is also determined by the processor in tracking the sensor. Thus the processor is able to calculate metrics of the location and orientation of distal end 34 by determining the location and orientation of sensor 32. The processor may position an icon corresponding to the location and orientation of the distal end on screen 56. In some embodiments, if the distal end is within patient 22, the external features of image 350 that may obscure the icon are rendered at least partially transparent.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. An apparatus, comprising:
   a rigid gripper configured to fasten around a cylindrical object;
      a pair of conductors attached to the gripper so as to make contact with one another, while the gripper is fastened around the cylindrical object, at a location along a length of the conductors that varies responsively to a diameter of the cylindrical object; and
   a sensing circuit configured to measure an impedance of a current passing through the pair of conductors and to generate an indication of the diameter responsively to the impedance,
   wherein the rigid gripper comprises a pair of jaws rotating about a common hinge so as to fasten around the cylindrical object, and wherein each of the conductors is attached to a respective jaw.

2. The apparatus according to claim 1, further comprising a sensor, fixedly attached to the rigid gripper, configured to generate a sensor signal indicative of a location of the gripper.

3. An apparatus, comprising:
   a rigid gripper configured to fasten around a cylindrical object;
      a pair of conductors attached to the gripper so as to make contact with one another, while the gripper is fastened around the cylindrical object, at a location along a length of the conductors that varies responsively to a diameter of the cylindrical object; and
   a sensing circuit configured to measure an impedance of a current passing through the pair of conductors and to generate an indication of the diameter responsively to the impedance,
   wherein the rigid gripper comprises a wedge configured to slide into an open rectangular frame so as to fasten about the cylindrical object, and wherein the pair of conductors comprises a first conductor attached to the frame, and a second conductor attached to the wedge.

4. The apparatus according to claim 3, wherein the second conductor comprises a pair of parallel conducting lines, and wherein the first conductor connects the parallel conducting lines.

5. A method, comprising:
   receiving a computerized tomography scan of a patient;
      registering an image of the patient derived from the scan with a magnetic tracking system configured to track a sensor in proximity to the patient;
      fixing the sensor to a rigid gripper configured to fasten around a cylindrical probe having a distal end;
      attaching a pair of conductors to the gripper so as to make contact with one another, while the gripper is fastened around the cylindrical probe, at a location along a length of the conductors that varies responsively to a diameter of the cylindrical probe;

measuring an impedance of a current passing through the pair of conductors and generating an indication of the diameter responsively to the impedance;

positioning the distal end in contact with the patient;

while the distal end is in contact with the patient, determining, responsively to the indication of the diameter, a vector representing a translation from the sensor to the distal end; and while tracking the sensor with the magnetic tracking system, adding the vector to a location of the sensor to determine a position of the distal end.

6. The method according to claim 5, and comprising determining a displacement from the sensor to the cylindrical probe responsively to the impedance, and further comprising determining the vector responsively to the displacement.

7. The method according to claim 5, and comprising determining a displacement from a point of contact of the distal end with the patient, along an axis of the cylindrical probe, to a region on the axis in proximity to the sensor, and further comprising determining the vector responsively to the displacement.

8. A method, comprising:
fastening a rigid gripper around a cylindrical object;
attaching a pair of conductors to the gripper so as to make contact with one another, while the gripper is fastened around the cylindrical object, at a location along a length of the conductors that varies responsively to a diameter of the cylindrical object;

measuring an impedance of a current passing through the pair of conductors and generating an indication of the diameter responsively to the impedance; and wherein the rigid gripper comprises a pair of jaws rotating about a common hinge so as to fasten around the cylindrical object, and wherein each of the conductors is attached to a respective jaw.

9. The method according to claim 8, and comprising fixedly attaching a sensor to the rigid gripper, wherein the sensor is configured to generate a sensor signal indicative of a location of the gripper.

10. A method, comprising:
fastening a rigid gripper around a cylindrical object;
attaching a pair of conductors to the gripper so as to make contact with one another, while the gripper is fastened around the cylindrical object, at a location along a length of the conductors that varies responsively to a diameter of the cylindrical object;

measuring an impedance of a current passing through the pair of conductors and generating an indication of the diameter responsively to the impedance; and wherein the rigid gripper comprises a wedge configured to slide into an open rectangular frame so as to fasten about the cylindrical object, and wherein the pair of conductors comprises a first conductor attached to the frame, and a second conductor attached to the wedge.

11. The method according to claim 10, wherein the second conductor comprises a pair of parallel conducting lines, and wherein the first conductor connects the parallel conducting lines.

12. An apparatus, comprising:
a cylindrical probe having a distal end;
a rigid gripper configured to fasten around the cylindrical probe;
a sensor, fixed to the rigid gripper, and configured to be tracked by a magnetic tracking system;
a pair of conductors attached to the gripper so as to make contact with one another, while the gripper is fastened around the cylindrical probe, at a location along a length of the conductors that varies responsively to a diameter of the cylindrical probe; and
a processor configured to:
receive a computerized tomography scan of a patient,
register an image of the patient derived from the scan with the magnetic tracking system,
measure an impedance of a current passing through the pair of conductors and generate an indication of the diameter responsively to the impedance,
while the distal end is in contact with the patient, determine, responsively to the indication of the diameter, a vector representing a translation from the sensor to the distal end, and
while tracking the sensor with the magnetic tracking system, add the vector to a location of the sensor to determine a position of the distal end.

13. The apparatus according to claim 12, and comprising configuring the processor to determine a displacement from the sensor to the cylindrical probe responsively to the impedance, and determine the vector responsively to the displacement.

14. The apparatus according to claim 12, and comprising configuring the processor to determine a displacement from a point of contact of the distal end with the patient, along an axis of the cylindrical probe, to a region on the axis in proximity to the sensor, and determine the vector responsively to the displacement.

* * * * *